(12) United States Patent
Widenhouse et al.

(10) Patent No.: US 8,206,294 B2
(45) Date of Patent: Jun. 26, 2012

(54) SURGICAL ACCESS DEVICE WITH FLEXIBLE SEAL CHANNEL

(75) Inventors: Christopher W. Widenhouse, Clarksville, OH (US); Frederick Earl Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 743 days.

(21) Appl. No.: 12/242,383

(22) Filed: Sep. 30, 2008

(65) Prior Publication Data

US 2010/0081871 A1 Apr. 1, 2010

(51) Int. Cl.
*A61B 1/32* (2006.01)
(52) U.S. Cl. ........................................................ 600/210
(58) Field of Classification Search ............. 604/164.08, 604/167.01–167.03, 167.06; 600/200–210, 600/104, 114, 117; 606/190–192
See application file for complete search history.

(56) References Cited

U.S. PATENT DOCUMENTS

| | | | |
|---|---|---|---|
| 2,129,391 A | 9/1938 | Wappler |
| 3,654,965 A | 4/1972 | Gramain |
| 4,112,932 A | 9/1978 | Chiulli |
| 4,306,545 A | 12/1981 | Ivan et al. |
| 4,402,683 A | 9/1983 | Kopman |
| 4,417,888 A | 11/1983 | Cosentino et al. |
| 5,183,464 A | 2/1993 | Dubrul et al. |
| 5,183,471 A | 2/1993 | Wilk |
| 5,197,955 A | 3/1993 | Stephens et al. |
| 5,207,213 A | 5/1993 | Auhll et al. |
| 5,209,737 A | 5/1993 | Ritchart et al. |
| 5,209,741 A | 5/1993 | Spaeth |
| 5,269,772 A | 12/1993 | Wilk |
| 5,285,945 A | 2/1994 | Brinkerhoff et al. |
| 5,308,336 A | 5/1994 | Hart et al. |
| 5,320,611 A | 6/1994 | Bonutti et al. |
| 5,366,478 A | 11/1994 | Brinkerhoff et al. |
| 5,385,553 A | 1/1995 | Hart et al. |
| 5,385,560 A | 1/1995 | Wulf |
| 5,391,154 A | 2/1995 | Young |
| 5,395,367 A | 3/1995 | Wilk |

(Continued)

FOREIGN PATENT DOCUMENTS

EP 0568383 11/1993

(Continued)

OTHER PUBLICATIONS

Gill IS, Canes D, Aron M, Haber GP, Goldfarb DA, Flechner S, Desai MR, Kaouk JH, Desai MM., "Single Port Transumbilical (E-NOTES) Donor Nephrectomy" Journal Urol., 180(2):637-41; Aug. 2008.

(Continued)

*Primary Examiner* — Eduardo C Robert
*Assistant Examiner* — Tara Carter
(74) *Attorney, Agent, or Firm* — Nutter McClennen & Fish LLP

(57) ABSTRACT

A surgical access device is provided that includes a housing having at least one access port therein for receiving a surgical instrument therethrough, and at least one elongate flexible instrument channel extending from the housing and having a lumen extending therethrough and in fluid communication with the at least one access port in the housing. The instrument channel is adapted to move from a first collapsed configuration in which the channel is sealed to substantially prevent fluid from flowing therethrough to a second expanded configuration upon insertion of an instrument therethrough.

24 Claims, 10 Drawing Sheets

U.S. PATENT DOCUMENTS

| | | | |
|---|---|---|---|
| 5,431,676 A | 7/1995 | Dubrul et al. |
| 5,443,452 A | 8/1995 | Hart et al. |
| 5,443,484 A | 8/1995 | Kirsch et al. |
| 5,480,410 A | 1/1996 | Cuschieri et al. |
| 5,492,304 A | 2/1996 | Smith et al. |
| 5,545,179 A | 8/1996 | Williamson, IV |
| 5,569,205 A | 10/1996 | Hart et al. |
| 5,569,254 A | 10/1996 | Carlson et al. |
| 5,584,850 A | 12/1996 | Hart et al. |
| 5,634,911 A | 6/1997 | Hermann et al. |
| 5,634,937 A | 6/1997 | Mollenauer et al. |
| 5,643,301 A | 7/1997 | Mollenauer |
| 5,653,705 A | 8/1997 | de la Torre et al. |
| 5,672,168 A | 9/1997 | de la Torre et al. |
| 5,676,657 A | 10/1997 | Yoon |
| 5,695,448 A | 12/1997 | Kimura et al. |
| 5,752,970 A | 5/1998 | Yoon |
| 5,782,812 A | 7/1998 | Hart et al. |
| 5,803,919 A | 9/1998 | Hart et al. |
| 5,814,058 A | 9/1998 | Carlson et al. |
| 5,827,319 A | 10/1998 | Carlson et al. |
| 5,865,807 A | 2/1999 | Blake, III |
| 5,891,013 A | 4/1999 | Thompson |
| 5,906,577 A | 5/1999 | Beane et al. |
| 5,957,913 A | 9/1999 | de la Torre et al. |
| 5,990,382 A | 11/1999 | Fox |
| 5,997,515 A | 12/1999 | de la Torre et al. |
| 6,004,303 A | 12/1999 | Peterson |
| 6,066,090 A | 5/2000 | Yoon |
| 6,077,288 A | 6/2000 | Shimomura et al. |
| 6,086,603 A | 7/2000 | Termin et al. |
| 6,120,513 A | 9/2000 | Bailey et al. |
| 6,123,689 A | 9/2000 | To et al. |
| 6,162,196 A | 12/2000 | Hart et al. |
| 6,217,555 B1 | 4/2001 | Hart et al. |
| 6,245,052 B1 | 6/2001 | Orth et al. |
| 6,258,069 B1 | 7/2001 | Carpentier et al. |
| 6,277,064 B1 | 8/2001 | Yoon |
| 6,315,770 B1 | 11/2001 | de la Torre et al. |
| 6,319,246 B1 | 11/2001 | de la Torre et al. |
| 6,328,730 B1 | 12/2001 | Harkrider, Jr. |
| 6,348,034 B1 | 2/2002 | Thompson |
| 6,352,503 B1 | 3/2002 | Matsui et al. |
| 6,440,061 B1 | 8/2002 | Wenner et al. |
| 6,447,489 B1 | 9/2002 | Peterson |
| 6,454,783 B1 | 9/2002 | Piskun |
| 6,458,077 B1 | 10/2002 | Boebel et al. |
| 6,551,270 B1* | 4/2003 | Bimbo et al. ............... 604/93.01 |
| 6,551,282 B1 | 4/2003 | Exline et al. |
| 6,589,167 B1 | 7/2003 | Shimomura et al. |
| 6,605,063 B2 | 8/2003 | Bousquet |
| 6,613,038 B2 | 9/2003 | Bonutti et al. |
| 6,669,674 B1 | 12/2003 | Macoviak et al. |
| 6,702,787 B2 | 3/2004 | Racenet et al. |
| 6,706,033 B1 | 3/2004 | Martinez et al. |
| 6,706,050 B1 | 3/2004 | Giannadakis |
| 6,807,965 B1 | 10/2004 | Hickle |
| 6,905,057 B2 | 6/2005 | Swayze et al. |
| 6,908,430 B2 | 6/2005 | Caldwell et al. |
| 6,939,296 B2 | 9/2005 | Ewers et al. |
| 6,945,932 B1 | 9/2005 | Caldwell et al. |
| 6,972,026 B1 | 12/2005 | Caldwell et al. |
| 7,014,628 B2 | 3/2006 | Bousquet |
| 7,052,454 B2 | 5/2006 | Taylor |
| 7,083,626 B2 | 8/2006 | Hart et al. |
| 7,118,528 B1 | 10/2006 | Piskun |
| 7,163,510 B2 | 1/2007 | Kahle et al. |
| 7,201,734 B2 | 4/2007 | Hickle |
| 7,214,185 B1 | 5/2007 | Rosney et al. |
| 7,247,154 B2 | 7/2007 | Hickle |
| 7,338,473 B2 | 3/2008 | Campbell et al. |
| 7,344,547 B2 | 3/2008 | Piskun |
| 7,393,322 B2 | 7/2008 | Wenchell |
| 7,413,559 B2 | 8/2008 | Stubbs et al. |
| 2002/0156432 A1 | 10/2002 | Racenet et al. |
| 2003/0028179 A1 | 2/2003 | Piskun |
| 2003/0139756 A1 | 7/2003 | Brustad |
| 2004/0015185 A1 | 1/2004 | Ewers et al. |
| 2004/0106942 A1 | 6/2004 | Taylor et al. |
| 2004/0138528 A1 | 7/2004 | Richter et al. |
| 2004/0199181 A1 | 10/2004 | Knodel et al. |
| 2004/0215063 A1 | 10/2004 | Bonadio et al. |
| 2004/0230160 A1 | 11/2004 | Blanco |
| 2004/0254426 A1 | 12/2004 | Wenchell |
| 2005/0020884 A1 | 1/2005 | Hart et al. |
| 2005/0033342 A1 | 2/2005 | Hart et al. |
| 2005/0085842 A1 | 4/2005 | Eversull et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0222582 A1 | 10/2005 | Wenchell |
| 2005/0267419 A1 | 12/2005 | Smith |
| 2005/0273132 A1 | 12/2005 | Shluzas et al. |
| 2005/0277946 A1 | 12/2005 | Greenhalgh |
| 2006/0019592 A1 | 1/2006 | Kupferberg et al. |
| 2006/0019723 A1 | 1/2006 | Vorenkamp et al. |
| 2006/0020241 A1 | 1/2006 | Piskun et al. |
| 2006/0020281 A1 | 1/2006 | Smith |
| 2006/0024500 A1 | 2/2006 | Seo |
| 2006/0071432 A1 | 4/2006 | Staudner |
| 2006/0212062 A1 | 9/2006 | Farascioni |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0241651 A1 | 10/2006 | Wilk |
| 2006/0241671 A1 | 10/2006 | Greenhalgh |
| 2006/0247500 A1 | 11/2006 | Voegele et al. |
| 2006/0247673 A1 | 11/2006 | Voegele et al. |
| 2006/0264706 A1 | 11/2006 | Piskun |
| 2006/0270978 A1 | 11/2006 | Binmoeller et al. |
| 2007/0049966 A1 | 3/2007 | Bonadio et al. |
| 2007/0060939 A1 | 3/2007 | Lancial et al. |
| 2007/0085232 A1 | 4/2007 | Brustad et al. |
| 2007/0088202 A1 | 4/2007 | Albrecht et al. |
| 2007/0088277 A1 | 4/2007 | McGinley et al. |
| 2007/0118021 A1 | 5/2007 | Pokorney |
| 2007/0151566 A1 | 7/2007 | Kahle et al. |
| 2007/0208312 A1 | 9/2007 | Norton et al. |
| 2007/0255219 A1 | 11/2007 | Vaugh et al. |
| 2007/0260121 A1 | 11/2007 | Bakos et al. |
| 2007/0260273 A1 | 11/2007 | Cropper et al. |
| 2008/0027476 A1 | 1/2008 | Piskun |
| 2008/0051739 A1 | 2/2008 | McFarlane |
| 2008/0065021 A1 | 3/2008 | Jenkins et al. |
| 2008/0119821 A1 | 5/2008 | Agnihotri et al. |
| 2008/0161826 A1 | 7/2008 | Guiraudon |
| 2008/0221389 A1 | 9/2008 | Beckman et al. |
| 2008/0255519 A1 | 10/2008 | Piskun et al. |
| 2009/0326465 A1* | 12/2009 | Richard ................... 604/167.01 |
| 2010/0081863 A1 | 4/2010 | Hess et al. |
| 2010/0081880 A1 | 4/2010 | Widenhouse et al. |

FOREIGN PATENT DOCUMENTS

| | | |
|---|---|---|
| EP | 0646358 | 4/1995 |
| EP | 950376 | 10/1999 |
| EP | 1350476 | 10/2003 |
| EP | 1498078 A1 | 1/2005 |
| EP | 1702575 A2 | 9/2006 |
| EP | 1731105 | 12/2006 |
| FR | 2710270 | 3/1995 |
| JP | 2006320750 | 11/2006 |
| WO | 2004075730 A2 | 9/2004 |
| WO | 2005087112 | 9/2005 |
| WO | 2005094432 | 10/2005 |
| WO | 2006019592 | 2/2006 |
| WO | 2006019723 | 2/2006 |
| WO | 2006035446 | 4/2006 |
| WO | 2007119232 | 10/2007 |
| WO | 2008024502 | 2/2008 |
| WO | 2008093313 | 8/2008 |
| WO | 2008149332 | 12/2008 |

OTHER PUBLICATIONS

Bucher P, Pugin F, Morel P., "Single Port Access Laparoscopic Right Hemicolectomy" Int J Colorectal Dis., Jul. 8, 2008.

Canes D, Desai MM, Aron M, Haber GP, Goel RK, Stein RJ, Kaouk JH, Gill IS., "Transumbilical Single-Port Surgery: Evolution and Current Status" Eur Urol., Jul. 14, 2008.

Goel RK, Kaouk JH., "Single Port Access Renal Cryoablation (SPARC): A New Approach" Eur Urol. Jun. 2008;53 (6):1204-9. Epub Mar. 18, 2008.

Kaouk JH, Palmer JS., "Single-port Laparoscopic Surgery: Initial Experience in Children for Varicocelectomy" BJU Int.;102(1):97-9. Epub Mar. 5, 2008.

Ponsky LE, Cherullo EE, Sawyer M, Hartke D., "Single Access Site Laparoscopic Radical Nephrectomy: Initial Clinical Experience" J Endourol., 22(4):663-6, Apr. 2008.

Ponsky TA, Lukish JR., "Single Site Laparoscopic Gastrostomy with a 4-mm Bronchoscopic Optical Grasper" J Pediatric Surgery, 43(2):412-4, Feb. 2008.

Rane A, Rao P, Rao P. Single-port-access Nephrectomy and Other Laparoscopic Urologic Procedures Using a Novel Laparoscopic Port (R-port), Urology. (2):260-3; discussion, Epub May 12, 2008.

Kaouk JH, Haber GP, Goel RK, Desai MM, Aron M, Rackley RR, Moore C, Gill IS., "Single-port Laparoscopic Surgery in Urology: Iniitial Experience", Urology., 71(1):3-6., Jan. 2008.

Vassallo C, Berbiglia G, Pessina A, Carena M, Firullo A, Griziotti A, Ramajoli F, Palamarciuc E, Fariseo M. "The Super-Magenstrasse and Mill Operation with Pyloroplasty: Preliminary Results", Obesity Surgery, Aug. 17, 2007.

Johnston D , Dachtler J , Sue-Ling Hm, King RF, Martin I. G, Roderick F.G. "The Magenstrasse and Mill Operation for Morbid Obesity" Obesity Surgery, Apr. 2003.

K. Sumiyama, C. Gostout, E.Rajan, T.Bakken, M.Knipschield, S.Chung, P.Cotton, R.Hawes, A.Kalloo, A.Kalloo, S. Kantsevoy and P.Pasricha "Transgastric Cholecystectomy: Transgastric Accessibility to the Gallbladder Improved with the SEMF Method and a Novel Multibending Therapeutic Endoscope" Gastrointestinal Endoscopy, vol. 65, Issue 7, Jun. 2007.

Web Page www.websurg.com/notes/videos.php <http://www.websurg.com/notes/videos.php>, Screenshots videos "Notes Hybrid Sleeve Gastrectomy Performed During Course" Vix, MD; Solano, MD; Asakuma, MD, Feb. 2008.

Web Page www.websurg.com/notes/videos.php <http://www.websurg.com/notes/videos.php>, Screenshots videos "Transvaginal Hybrid Notes Sleeve Gastrectomy Porcine Model" Vix, MD; Solano, MD; Asakuma, MD, Dec. 2007.

Ahmad G, Duffy JM, Phillips K, Watson A., "Laparoscopic Entry Techniques" Cochrane Database Syst Rev., (2): CD006583, Apr. 16, 2008.

EP Search Report #09252308.3, Feb. 2, 2010.

Product Brochure "Access the Future of Laparoscopic Surgery" Advanced Surgical Concepts Limited, Inc., dated no later than Aug. 26, 2008 (date of download from Advanced Surgical Concepts Limited, Inc. website at http://www.advancedsurgical.ie/TriPort/Default.166.html).

* cited by examiner

SURGICAL ACCESS DEVICE WITH FLEXIBLE SEAL CHANNEL

FIELD OF THE INVENTION

The present invention relates to surgical access devices for providing access into a body cavity.

BACKGROUND OF THE INVENTION

Abdominal laparoscopic surgery gained popularity in the late 1980's, when benefits of laparoscopic removal of the gallbladder over traditional (open) operation became evident. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall.

Laparoscopic procedures generally involve insufflation of the abdominal cavity with $CO_2$ gas to a pressure of around 15 mm Hg. The abdominal wall is pierced and a 5-10 mm in diameter straight tubular cannula or trocar sleeve is then inserted into the abdominal cavity to create a channel into the body. A laparoscopic telescope connected to an operating room monitor is used to visualize the operative field, and is placed through a the trocar sleeve. Laparoscopic instruments (graspers, dissectors, scissors, retractors, etc.) are placed through two or more additional trocar sleeves for the manipulations by the surgeon and surgical assistant(s). While it is necessary to create channels into the body in order to perform procedures, it is also necessary to maintain a seal through the devices to prevent unwanted fluid and other materials from passing through the channel formed into the body cavity.

Accordingly, there is a need for improved methods and devices for providing access into a body cavity while maintaining a seal therethrough.

SUMMARY OF THE INVENTION

The present invention provides various devices and methods for providing access to a body cavity. In one embodiment, a surgical access device is provided and includes a housing having at least one access port therein for receiving a surgical instrument therethrough, and at least one elongate flexible instrument channel extending from the housing. The instrument channel has a lumen extending therethrough and in fluid communication with the at least one access port in the housing. In an exemplary embodiment, the instrument channel is adapted to move from a first collapsed configuration in which the channel is sealed to substantially prevent fluid from flowing therethrough to a second expanded configuration upon insertion of an instrument therethrough. The elongate instrument channel can be in a natural resting state in the first collapsed configuration. The device can also include a retractor coupled between the housing and the instrument channel and including an opening extending therethrough and first and second flanges configured to engage tissue therebetween. The housing can have various configurations, and can include a plurality of access ports therein. Each access port can optionally include an elongate flexible instrument channel extending therefrom. Each access port can also include a seal therein that is configured to form a seal around an instrument inserted therethrough and/or seal the access port when no instrument is inserted therethrough.

The instrument channel can have various configurations. In one embodiment, the elongate instrument channel can be twisted in the first collapsed configuration and untwisted in the second expanded configuration. In another embodiment, the elongate instrument channel can be curled longitudinally in the first collapsed configuration and straightened in the second expanded configuration. The instrument channel can also have various shapes, such as a substantially planar cross section in the first collapsed configuration. The instrument channel can also include various additional features, such as at least one sealing element disposed therein and configured to form a seal around an instrument inserted therethrough. The instrument channel can also include at least one stiffening element extending longitudinally therethrough and configured to provide longitudinal strength to the channel for preventing inversion of the channel while allowing for radial flexibility of the channel. The instrument channel can also form a seal around instruments of various diameters.

In another embodiment, a surgical access device is provided and includes a housing having an access port extending therethrough for receiving a surgical instrument, and an elongate flexible instrument channel extending from the housing and having an inner lumen extending longitudinally therethrough and in communication with the access port in the housing. In one embodiment, the inner lumen can include at least one stiffening element extending longitudinally along the channel and configured to provide longitudinal strength to the channel for preventing inversion of the channel while allowing for radial flexibility of the channel. The at least one stiffening element can extend from a distal end to a proximal end of the elongate instrument channel along or within a wall of the elongate instrument channel. The stiffening element can have a variety of configurations. For example, the at least one stiffening element can be in the form of at least one longitudinally-extending surface feature, or at least one wire or spring disposed within a longitudinal groove formed in the channel.

The elongate instrument channel can be adapted to move from a first collapsed configuration in which the channel is sealed to substantially prevent fluid from flowing therethrough to a second expanded configuration upon insertion of an instrument therethrough. The device can also include a retractor coupled between the housing and the instrument channel and including an opening extending therethrough. The retractor can have first and second flanges configured to engage tissue therebetween. The housing can include a plurality of access ports therein, and each access port can optionally include an elongate flexible instrument channel extending therefrom.

Methods for accessing a body cavity are also provided, and in one embodiment the method can include forming an access hole through tissue, and positioning a housing on a surface of the tissue such that an elongate flexible instrument channel coupled to the housing extends into the body cavity. Positioning the housing can include positioning a flexible retractor coupled between the housing and the channel in the access hole in the tissue to retract the tissue. The method can further include inserting an instrument through an access port in the housing and through the elongate instrument channel to move the channel from a natural resting state in which the channel is in a first collapsed sealed configuration to a second expanded configuration. The instrument channel can move to the second expanded configuration in a variety of ways. For example, the elongate flexible instrument channel can untwist as it is moved to the second expanded configuration, or can unroll as it is moved to the second expanded configuration. In one embodiment, the method can include removing the instrument from the channel. The channel can, for example, twist or curl as the instrument is removed. In one exemplary embodiment, the instrument can be inserted into a second access port in the housing and through a second elongate flexible instrument channel to move the channel from a first collapsed configuration in which the channel is sealed to substantially prevent fluid from flowing therethrough to a second expanded configuration.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides various methods and device for accessing a body cavity. In general, a surgical access device is provided that includes an elongate flexible instrument channel that is adapted to move between a first collapsed configuration in which the channel is sealed to prevent fluid flow therethrough and a second expanded configuration upon insertion of an instrument therethrough. In the expanded configuration, while not necessary, the channel can form a seal around the instrument. The flexible instrument channel can be in a resting state in the first configuration such that the channel is self-sealing when no instrument is inserted therethrough. The use of a self-sealing channel can eliminate the need for additional sealing elements in the access port, thereby allowing for a reduced-profile housing and a lower cost housing. However, additional sealing elements may still be used in conjunction with the self-sealing channel. For example, while the channel forms a seal when no instrument is inserted therethrough, it may be desirable to have an instrument seal in the access port and/or in the channel that forms a seal around an instrument inserted therethrough. The use of a self-sealing channel can also be advantageous in an access device having multiple access ports as the channel or a separate sealing element in the channel can maintain a seal around an instrument inserted therethrough while the instrument is being flexed and manipulated in various directions. In addition, the self-sealing channel can accommodate surgical instruments therethrough having various sizes as the channel can collapse around the instrument to form a seal therearound. For example, a seal can be formed around instruments that range in diameter from 5 mm to 15 mm.

Figure 1:
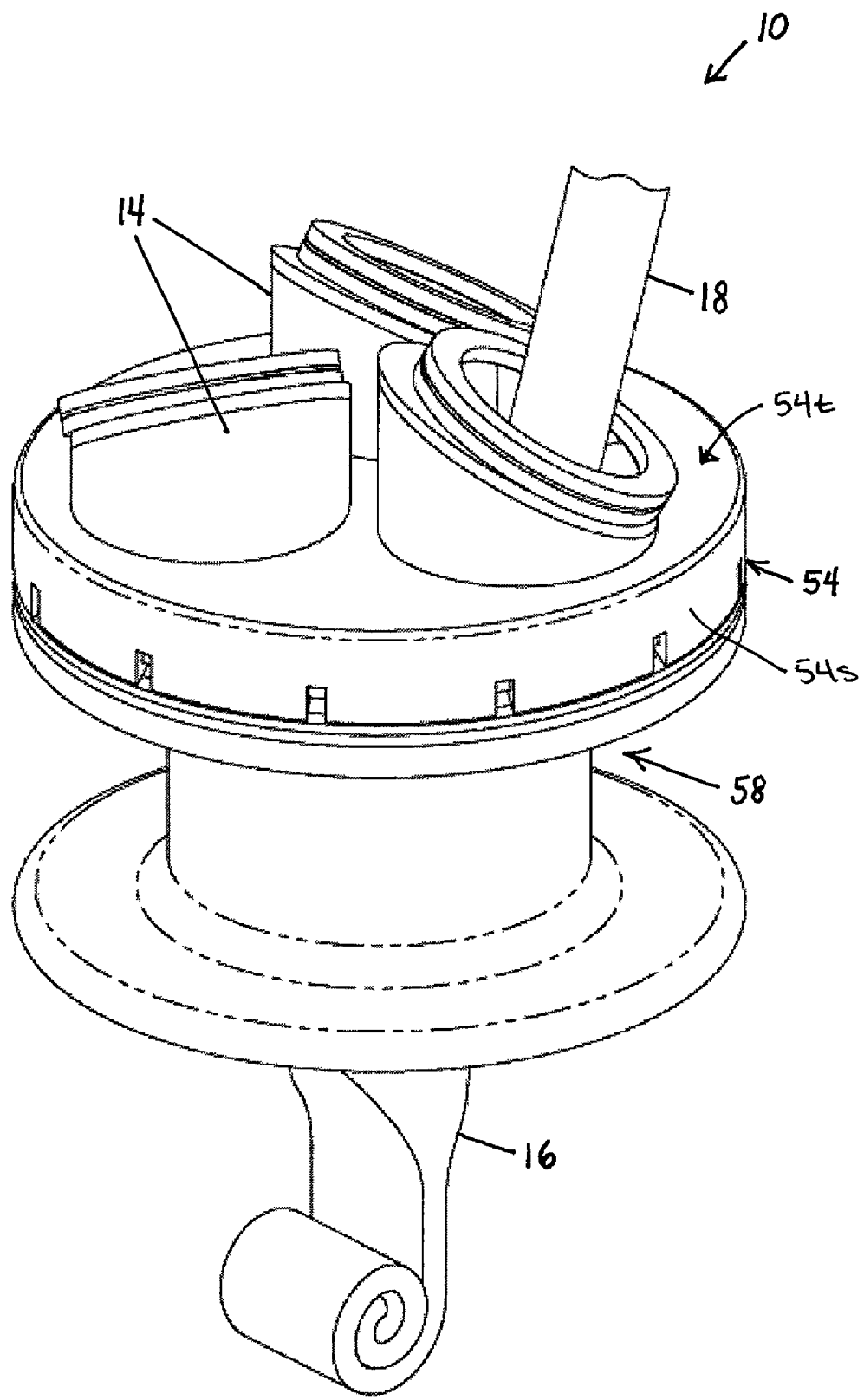
FIG. 1 is a perspective view of one embodiment of a surgical access device having an elongate flexible instrument channel extending therefrom and shown in a first collapsed configuration with a surgical instrument about to be inserted therethrough.
Figure 2:
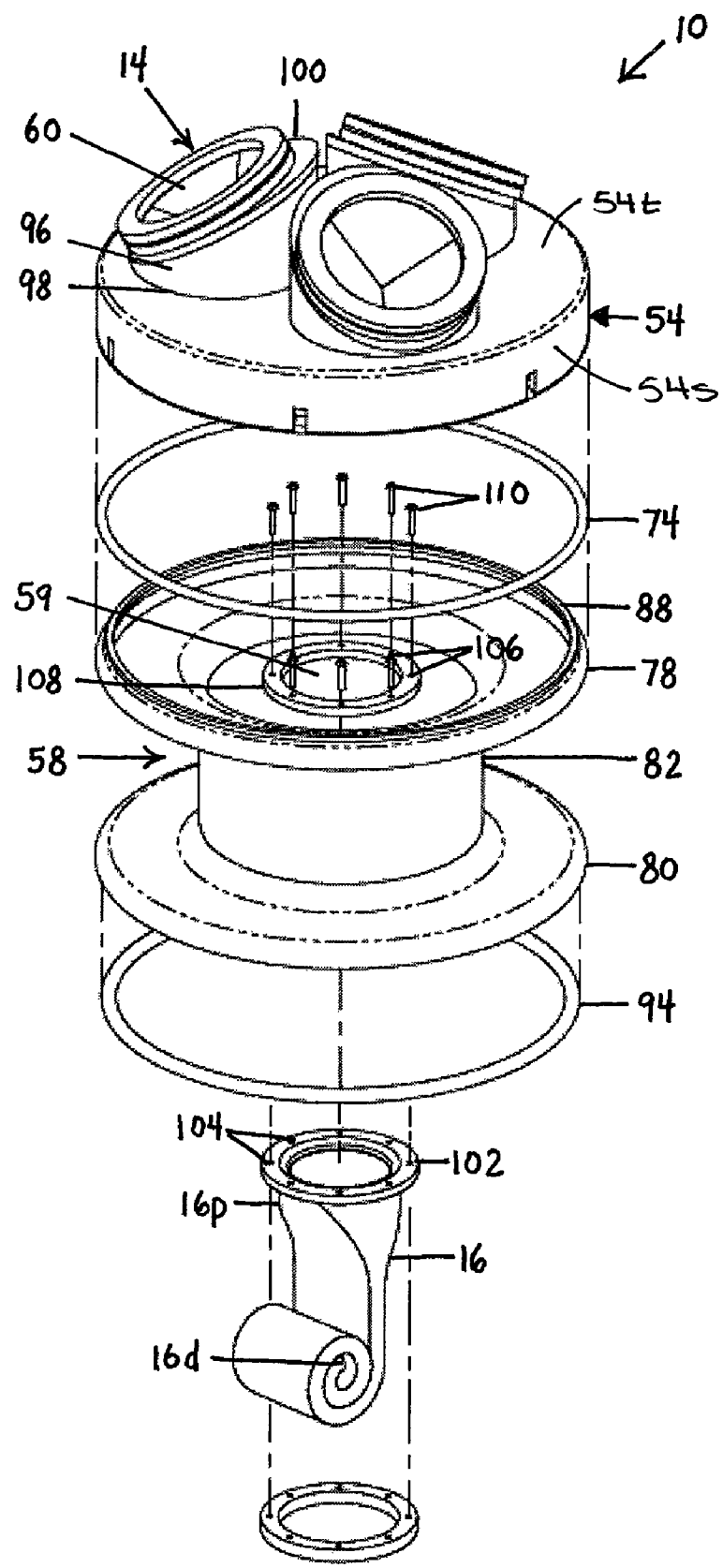
FIG. 2 is an exploded perspective view of the surgical access device of FIG. 1.
Figure 3:
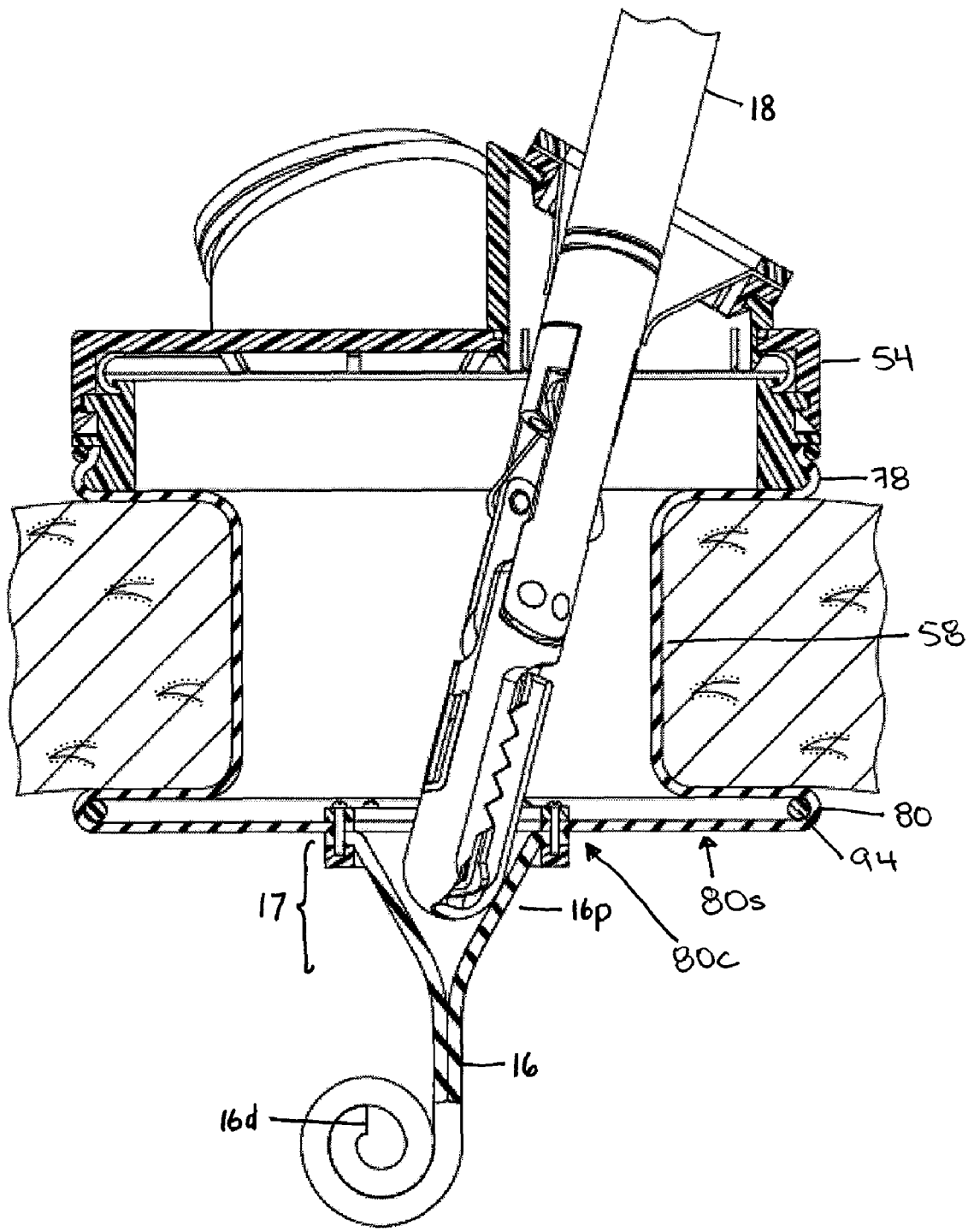
FIG. 3 is a cross-sectional view of the surgical access device and instrument of FIG. 1.
Figure 4:
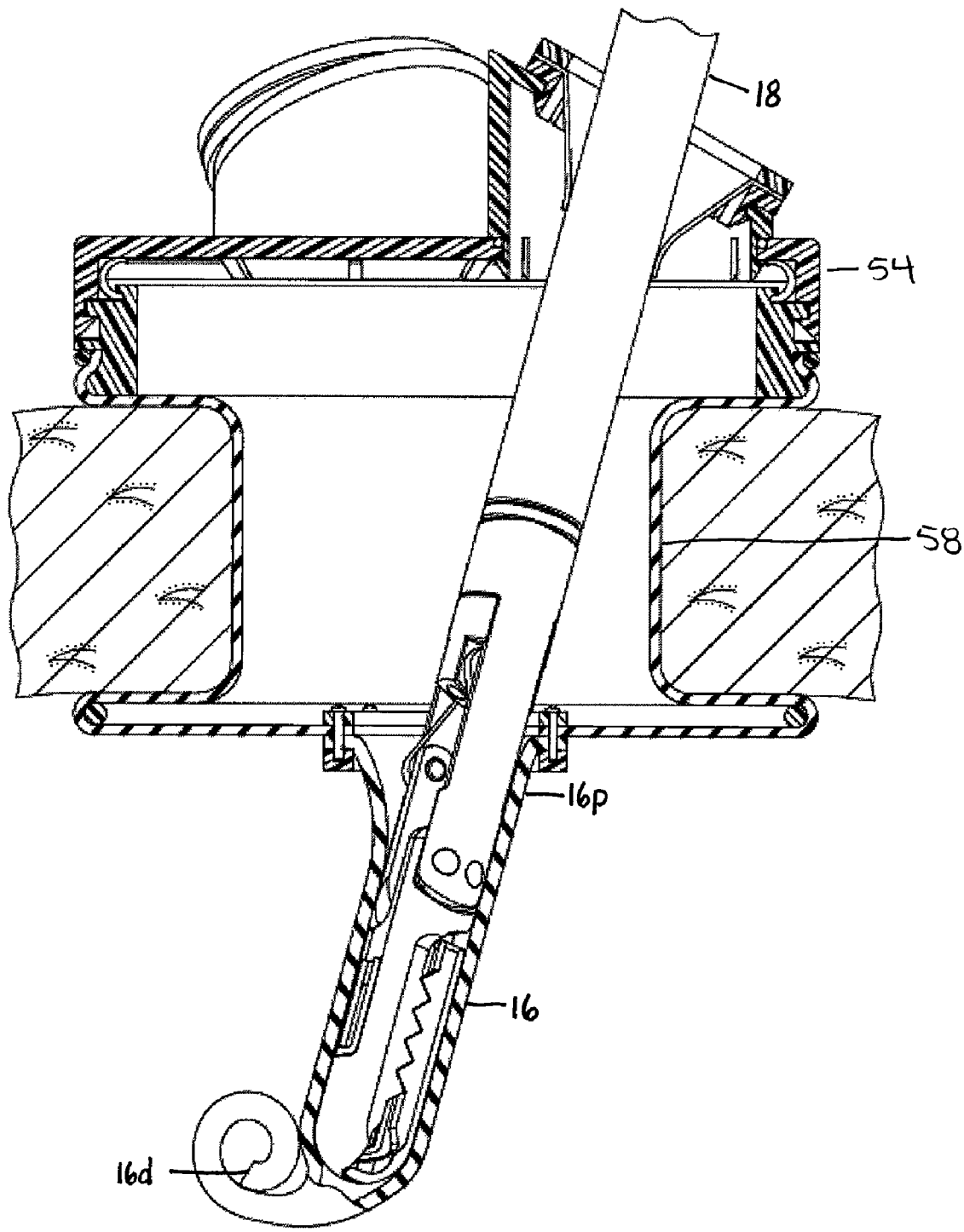
FIG. 4 is a cross-sectional view of the surgical access device and instrument of FIG. 3 showing the instrument advanced to move the channel from the first collapsed configuration to a second expanded configuration.
Figure 5:
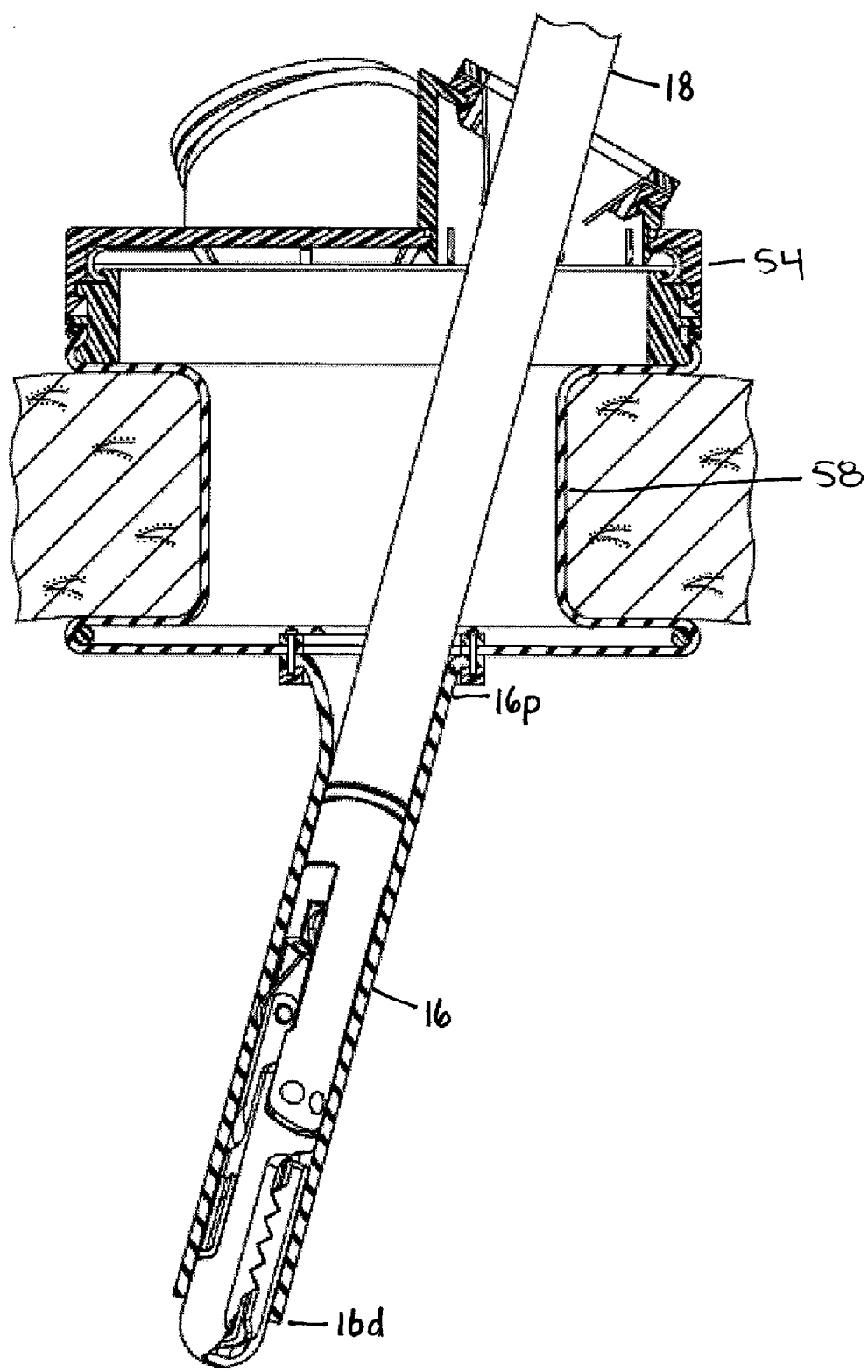
FIG. 5 is a side view of the surgical access device and instrument of FIG. 4 with the surgical instrument fully inserted through the channel to move the channel into the second expanded configuration.

FIGS. 1-5 illustrate one exemplary embodiment of a surgical access device 10 that generally includes a housing 54 having at least one access port 14 therein for receiving a surgical instrument 18 therethrough, and at least one elongate flexible instrument channel 16 extending therefrom and having an inner lumen extending therethrough. The inner lumen in the instrument channel 16 is in fluid communication with the access port 14 of the housing 54 to allow the surgical instrument 18 to pass through the access port 14 and into the inner lumen of the instrument channel 16. The instrument channel 16 is adapted to move from a natural resting state in a first collapsed configuration in which the instrument channel 16 is substantially sealed, as shown in FIGS. 1-3, to a second expanded configuration upon insertion of the surgical instrument 18 therethrough, as shown in FIGS. 4-5.

The housing 54 of the surgical access device 10 can have a variety of configurations, and the instrument channel 16 can extend from any housing having an opening therethrough for providing access to a body cavity. In the embodiment illustrated in FIGS. 1-5, the housing 54 is substantially rigid and has a cylindrical shape with a planar top surface 54t and a sidewall 54s extending distally from the top surface 54t. A housing o-ring 74, which can be flexible or rigid as needed, can be disposed within the sidewall 54s of the housing 54 to form a seal between the housing 54 and a retractor 58, which is discussed in more detail below. In one embodiment, the housing 54 can be threadedly secured to the retractor 58 via mating of threads formed on the housing 54 and the retractor 58 such that the housing o-ring 74 is secured therebetween. A person skilled in the art will appreciate that various other techniques can be used to mate the housing 54 to the retractor 58, such as a snap-fit or other mechanical interlock. The housing 54 and the retractor 58 can also fixedly mate to one another, or they can rotatably mate to one another. In other embodiments, various portions of the housing 54 can be flexible. Such flexibility can not only help to maintain a seal around instruments disposed therethrough as the instruments are being manipulated into various angular orientations, but it can also allow a broader range of movement of instruments inserted therethrough thus facilitating better positioning of the instruments relative to a target site.

The housing 54 can include multiple access ports formed in the top surface 54t thereof. While any number of access ports 14 can be formed in the housing 54, in the embodiment shown in FIGS. 1-2, three access ports 14 extend through the surgical access device 10. In general, each access port 14 can include a port housing 96 which can be fixedly or freely rotatably seated within a port opening formed in the top surface 54t of the housing 54. The port housing 96 can have any shape, height, or angular configuration, but in the embodiment shown in FIGS. 1-5, the port housing 96 has a cylindrical shape with a planar distal end 98 that couples to the top surface 54t of the housing 54, and a proximal end 100 that extends at an angle relative to the top surface 54t of the housing 54. The angle at which the proximal end 100 extends can determine the entry angle for an instrument inserted therethrough, as will be discussed further below. Each access port 14 can also have a sealing element 60 disposed therein and configured to form a seal around an instrument inserted therethrough. Various types of sealing elements can be used. By way of non-limiting example, the sealing element can be an instrument seal that forms a seal around an instrument but otherwise does not form a seal when no instrument is inserted therethrough, a channel seal or zero-closure seal that forms a seal when no instrument is inserted therethrough, or a combination seal that both seals the working channel when no instrument is inserted therethrough and forms a seal around instruments inserted therethrough. Exemplary seals include flapper valves, duckbill seals, conical seals, multi-layer seals, diaphragm seals, gel seals, etc. In certain exemplary embodiments, the sealing element is an instrument seal, such as a multiple layer seal. The sealing elements 60 can also extend in various planes that are different from one another as determined by the angular orientation of the proximal end 100 of the port housing 96.

Other exemplary embodiments of access devices are disclosed in U.S. patent application Ser. No. 12/242765 filed on even date herewith and entitled "Surgical Access Device," which is hereby incorporated by reference in its entirety. A person skilled in the art will appreciate that any of the various embodiments disclosed in the aforementioned application can be used in any combination with the present invention.

As noted above, a retractor 58 can extend from the housing 54, and in one embodiment, the retractor 58 is a substantially flexible member having a proximal flange 78 and a distal flange 80 with an inner elongate portion 82 extending therebetween. An opening 59 extends through the proximal flange 78, the inner elongate portion 82, and the distal flange 80 of the retractor 58 to define a pathway for receiving surgical instruments. As discussed above, the proximal flange 78 can be configured to mate to the housing 54 using various techniques, such as by an adhesive, sealant, or any other attachment mechanism known in the art. The o-ring 74 can be positioned between the retractor 58 and the housing 54 to help form a seal therebetween. The retractor 58 can also include a rigid o-ring 94 that can be disposed within the distal flange 80 thereof and can be configured to maintain the shape of the distal flange 80 of the retractor 58. Such support may be necessary where the channel 16 mates to a distal support surface 80s of the retractor 58, as shown in FIG. 3. The support surface 80s can extend longitudinally across the opening 59 of the retractor 58, and it can include a central opening 80c formed therein for allowing fluid communication between the opening 59 in the retractor 58 and the channel 16.

The instrument channel 16 extends distally from the retractor 58 and is in fluid communication with at least one of the access ports 14 of the housing 54 via the opening 59 in the retractor 58. The channel 16 can be coupled to the retractor 58 or the housing 54 in a variety of ways. In the illustrated embodiment, the instrument channel 16 includes a first mating ring 102 on a proximal end 16p thereof that is positioned adjacent to a distal surface of the support surface 80s of the retractor 58 and circumferentially around the central opening 80c. The first mating ring 102 can be coupled to the instrument channel 16 in a variety of ways. For example, the mating ring 102 can be formed on the proximal end 16p of instrument channel 16 or can be coupled thereto using any technique known in the art. The mating ring 102 can include a plurality of holes 104 formed therein that correspond to holes 106 formed in a second mating ring 108 disposed on a proximal surface of the support surface 80s of the retractor 58. The first and second mating rings 102, 108 can engage the support surface 80s around the opening 80c and mate to one another to mate the channel 16 to the retractor 58. A plurality of pins or screws 110 can be used to extend through the holes 104, 106 formed in both mating rings 102, 108 in order to mate the mating rings 102, 108 to one another and formed a seal therebetween. A person skilled in the art will appreciate, however, that the mating rings 102, 108 can be mated together using any technique known in the art, and that various other techniques can be used to mate or integrally form the channel 16 with the retractor 58. Moreover, the channel 16 can be mated to a proximal portion of the retractor 58 or to the housing 54. The instrument channel 16 can be coupled to any component of the device 10 in any manner that allows the instrument channel 16 to be in fluid communication with at least one of the access ports 14.

As explained above, the instrument channel is adapted to move between a first collapsed configuration and a second expanded configuration upon insertion of a surgical instrument therethrough. The instrument channel can be in a natural resting state in the first collapsed configuration, in which the channel is closed and sealed to substantially prevent fluid or any other material from flowing therethrough. During insertion of an instrument through the channel to move the channel from the first collapsed configuration to the second expanded configuration, the instrument channel can open and expand, however it may still collapse around the surgical instrument to create a seal around the surgical instrument. A person skilled in the art will appreciate that the instrument channel can have any configuration that allows for movement between a first configuration in which the instrument channel is sealed, and a second configuration in which a surgical instrument extends through the instrument channel.

In the embodiment illustrated in FIGS. 1-5, the instrument channel 16 is curled longitudinally in the first collapsed configuration, and is straightened in the second expanded configuration. The instrument channel 16 can be curled along the entire length thereof, or can be curled along portions, e.g., from a distal end 16d to a location distal of the proximal end 16p of the instrument channel 16, as illustrated in FIGS. 1-3. The instrument channel 16 can also include a non-curled tapered region 17 in a proximal end thereof to increase the ease of inserting a surgical instrument 18 therethrough. The tapered region 17 can decrease in diameter in a proximal-to-distal direction. The instrument channel 16 can have a variety of configurations, but in the illustrated embodiment is in the form of a flexible elongate tube having a substantially rectangular cross sectional shape. In particular, the instrument channel 16 is formed from two substantially planar surfaces having opposed sidewalls formed therebetween. In the first collapsed configuration, the planar surfaces are substantially adjacent one another to achieve a seal through the instrument channel 16. In the second expanded configuration, the planar surfaces of the instrument channel 16 expand outward between the opposed sidewalls as a surgical instrument 18 moves therethrough, thus creating space therein for the instrument 18. The instrument channel 16 is adapted to extend into a body cavity and thus can have a length sufficient to allow the distal end 16d of the instrument channel 16 to be positioned within the body while the proximal end 16p can coupled to the access device 10. The instrument channel 16 can be formed from a variety of materials, including a variety of biocompatible materials that have properties sufficient to enable the instrument channel 16 to be inserted into the body.

In the natural resting state, as shown in FIG. 3, the curled channel 16 achieves a seal to prevent fluid flow therethrough. As a surgical instrument 18 is passed through the curled instrument channel 16, as shown in FIG. 4, the instrument channel 16 is uncurled by the surgical instrument 18 as it is moved distally through the instrument channel 16. Any portion distal of the distal end of the surgical instrument 18 will remain curled to maintain a seal in the instrument channel 16. While not necessary, the instrument channel 16 can also collapse around the surgical instrument 18 as it is passed therethrough to form a seal therearound to continue to prevent fluid or other materials from passing through the instrument channel 16. The surgical instrument 18 can be passed through the instrument channel 16 until a distal end of the surgical instrument 18 extends from the distal end 16d of the instrument channel 16 to allow the surgical instrument 18 access to the body cavity, as shown in FIG. 5. When the surgical instrument 18 is removed from the instrument channel 16, the instrument channel 16 can being to curl at its distal end 16d, and will continue to curl up to a location just distal of the location of the surgical instrument 18 as the surgical instrument 18 moves proximally out of the instrument channel 16.

Figure 6:
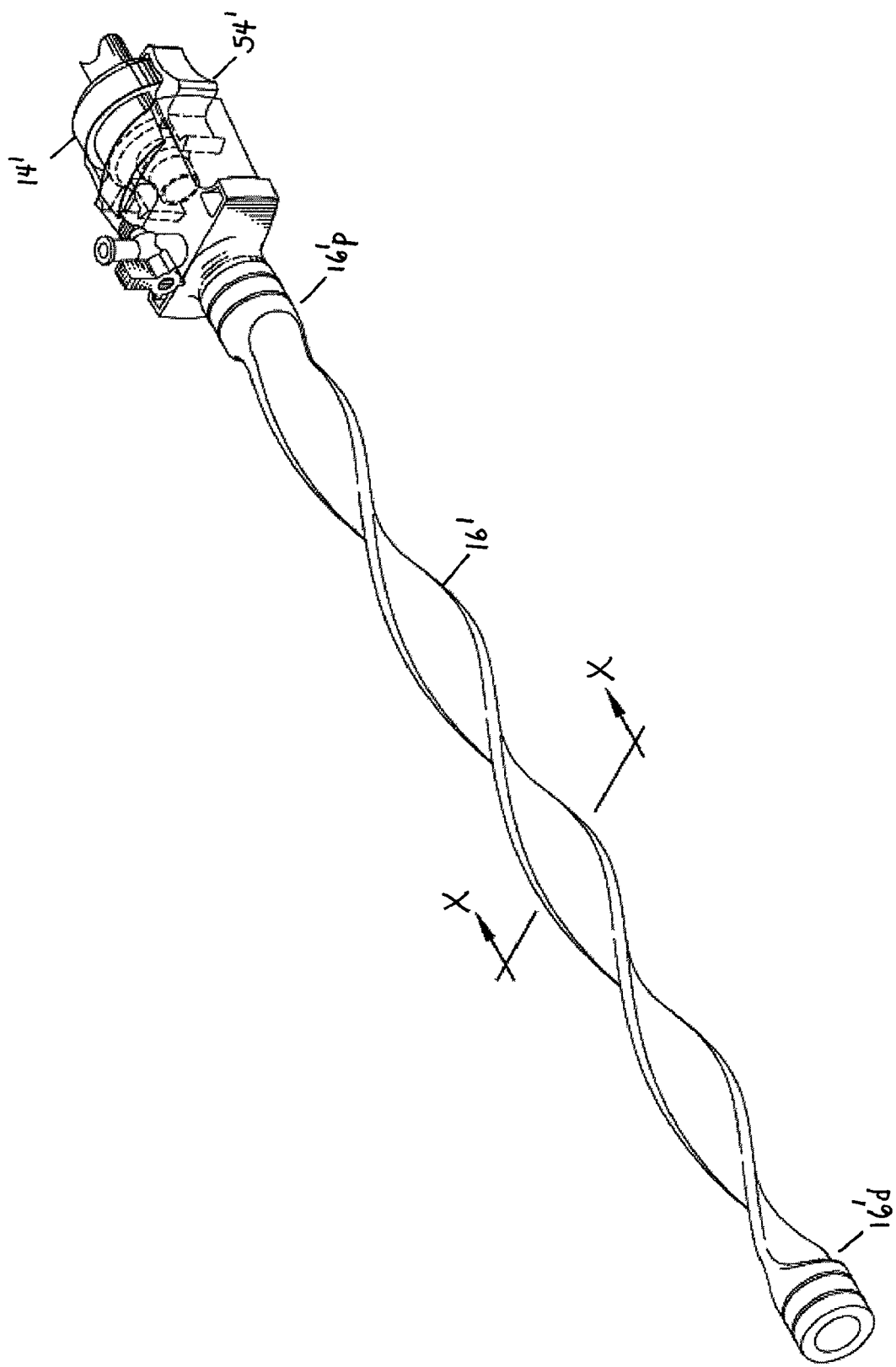
FIG. 6 is a perspective view of another embodiment of an elongate flexible instrument channel extending from a surgical access device.

In another exemplary embodiment, illustrated in FIG. 6, an instrument channel 16' can extend from a housing 54' that includes a single access port 14' formed therein. A person skilled in the art will appreciate, however, that the instrument channel 16' can extend from any housing with any number of ports, including the housing 54 shown in FIGS. 1-5. The instrument channel 16' is twisted in the first collapsed configuration, and is untwisted in the second expanded configuration. The instrument channel 16' can be twisted along the entire length thereof, as illustrated in FIG. 6, or it can be twisted along portions, e.g., from a distal end 16'p to a location distal of the proximal end 16'p of the instrument channel 16'. The instrument channel 16' can be in its natural resting state when twisted, as shown in FIG. 6, to achieve a seal to prevent fluid flow therethrough. The instrument channel 16' can have a variety of configurations, but in the illustrated embodiment is in the form of a flexible elongate tube having a substantially planar cross section that is twisted in the first collapsed configuration such that opposed planar surfaces of the instrument channel 16' are substantially adjacent one another to achieve a seal through the instrument channel 16'. In the second expanded configuration, the opposed planar surfaces of the instrument channel 16' are configured to untwist and expand outward as a surgical instrument moves therethrough, thus creating space therein for the instrument. Similar to instrument channel 16, instrument channel 16' is adapted to extend into a body cavity and thus can have a length sufficient to allow the distal end 16'd of the instrument channel 16' to be positioned within the body while the proximal end 16'p can be coupled to the surgical access device. The instrument channel 16' can be formed from a variety of materials, including a variety of biocompatible materials that have properties sufficient to enable the instrument channel 16' to be inserted into the body.

Similar to instrument channel 16, instrument channel 16' is untwisted by a surgical instrument as it is moved distally through the instrument channel 16', but remains twisted proximal of the surgical instrument to maintain the seal of the instrument channel 16'. The instrument channel 16' can also collapse around the surgical instrument as it is passed therethrough to form a seal therearound to continue to prevent fluid or other materials from passing through the instrument channel 16'. When the surgical instrument is passed through the instrument channel 16' until a distal end of the surgical instrument extends from the distal end 16'd of the instrument channel 16' and into a body cavity, the instrument channel 16' is fully untwisted along its entire length and can be collapsed around the surgical instrument to form a seal along an entire length thereof. When the surgical instrument is removed from the instrument channel 16', the instrument channel 16' can being to twist at its distal end 16'd, and will continue to twist up to a location just distal of the location of the surgical instrument as the surgical instrument moves proximally out of the instrument channel 16'.

Figure 7:
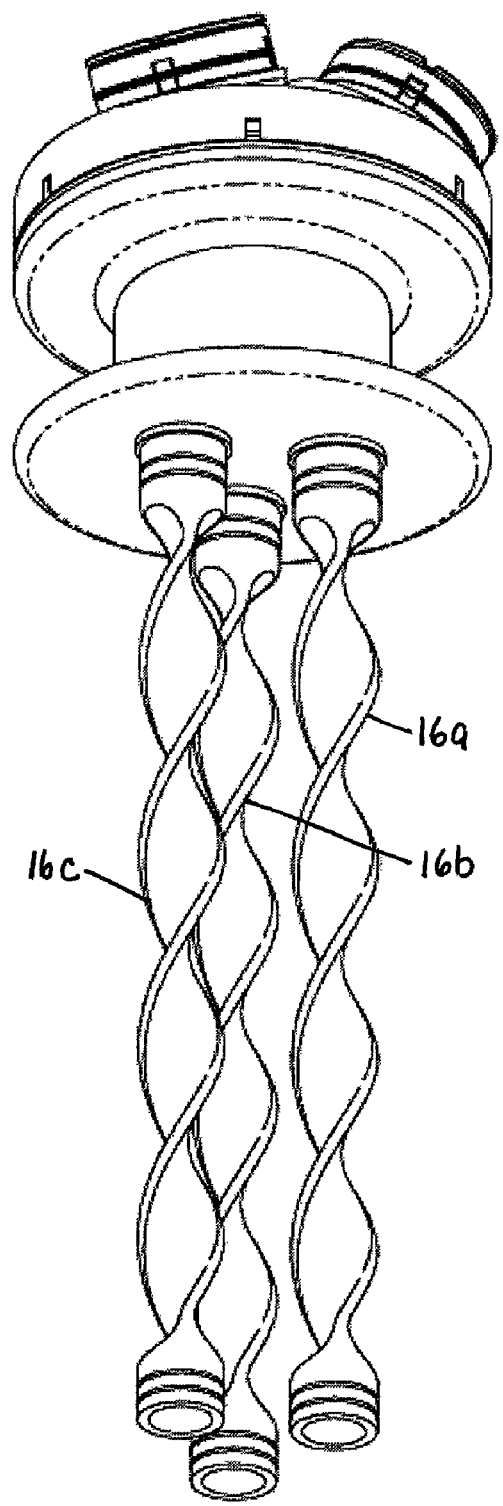
FIG. 7 is a perspective view of yet another embodiment of a surgical access device having a plurality of elongate flexible instrument channels extending therefrom.
Figure 8:
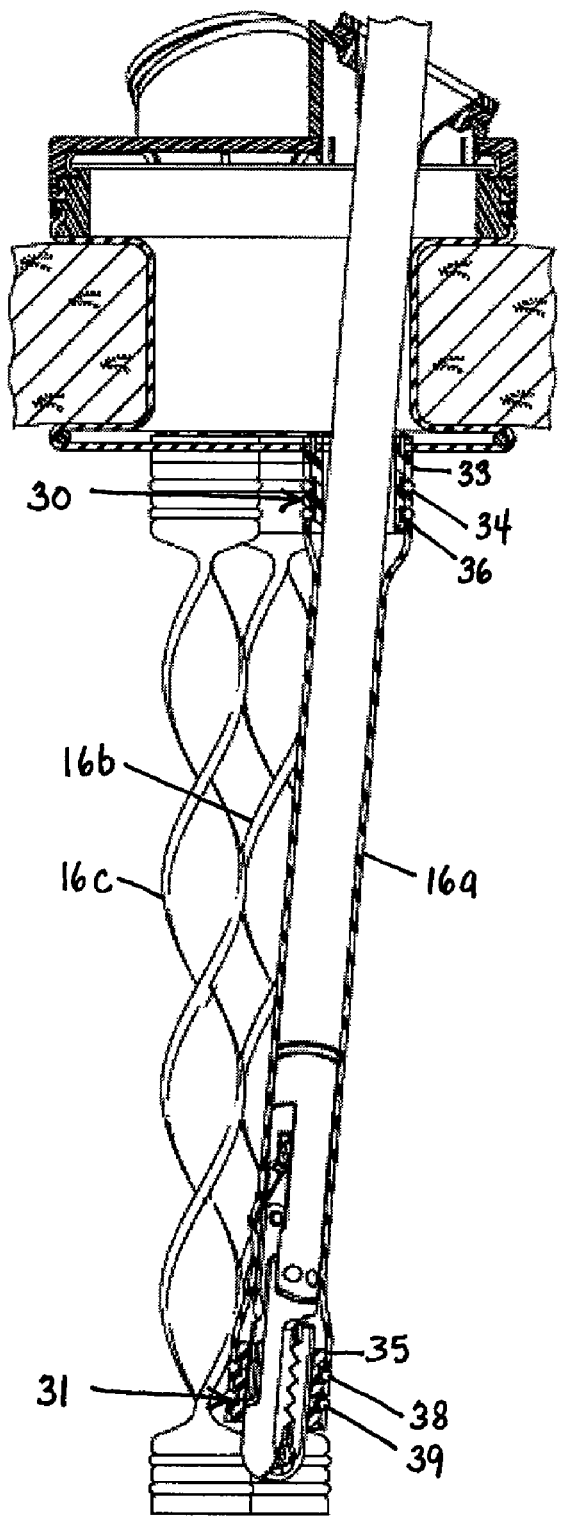
FIG. 8 is a partially cross-sectional view of the surgical access device of FIG. 7 showing a surgical instrument extending through one of the plurality of elongate flexible instrument channels.

It may be advantageous to have more than one surgical instrument with access to a body cavity at a given time. In order to accommodate multiple surgical instruments, in one embodiment multiple instrument channels can extend from multiple access ports. In the embodiment illustrated in FIGS. 7-8, three instrument channels 16a, 16b, 16c extend from a housing and are in fluid communication with the access ports disposed therein to provide multiple surgical instruments access into a body cavity simultaneously. While FIGS. 7-8 illustrate instrument channels 16a, 16b, 16c that are in a twisted configuration, a person skilled in the art will appreciate that any type of instrument channel, including the curled configuration shown in FIGS. 1-5, can be used and in any combination thereof. A person skilled in the art also will appreciate that any number of instrument channels can be used to allow for any number of surgical instruments to be passed through the device 10 for access to a body cavity.

The instrument channel can also optionally include features to aid in sealing the instrument channel. While many configurations are possible, in the embodiment illustrated in FIG. 8, one or more sealing elements can be disposed in the instrument channels 16a, 16b, 16c, for example, in the proximal and/or distal ends of the instrument channels 16a, 16b, 16c and the sealing elements can be configured to form a seal around an instrument inserted therethrough and/or to seal the instrument channels 16a, 16b, 16c. The sealing elements 30, 31 can have a variety of configurations, but in the illustrated embodiment are in the form of two o-rings 34, 36 that are disposed within a proximal housing 33 of the channel 16a and two o-rings 38, 39 that are disposed within a distal housing 35 of the channel 16a. The o-rings 34, 36, 38, 39 are configured to engage an instrument inserted therethrough. A person skilled in the art will appreciate, however, that any number of o-rings can be disposed within the channels to form a seal around an instrument inserted therethrough, and that various other types of sealing elements can be disposed in the instrument channel in any location that is desired to facilitate sealing of the instrument channel around an instrument. Moreover, a person skilled in the art will appreciate that sealing elements can be used with any embodiment of the instrument channels disclosed herein, including instrument channel 16 shown in FIGS. 1-5 and instrument channel 16' shown in FIG. 6.

Figure 9:
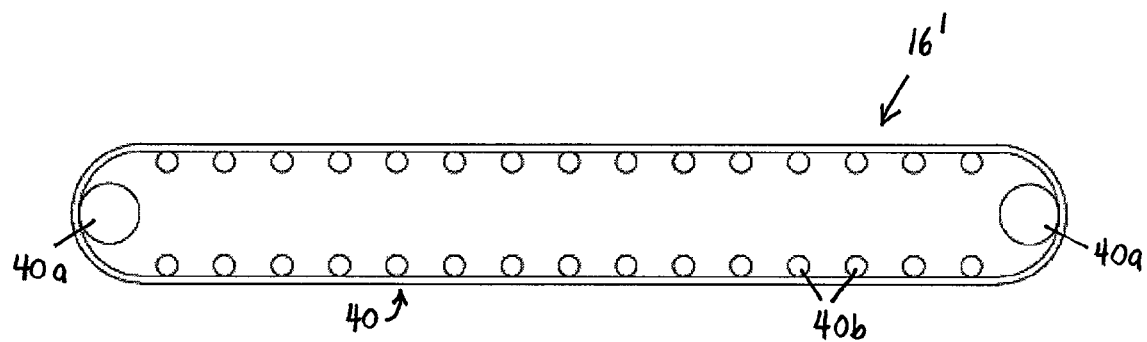
FIG. 9 is a cross-sectional view taken across line X-X of the instrument channel of FIG. 6 in a first collapsed configuration showing one embodiment of a plurality of stiffening elements extending therethrough.
Figure 10:
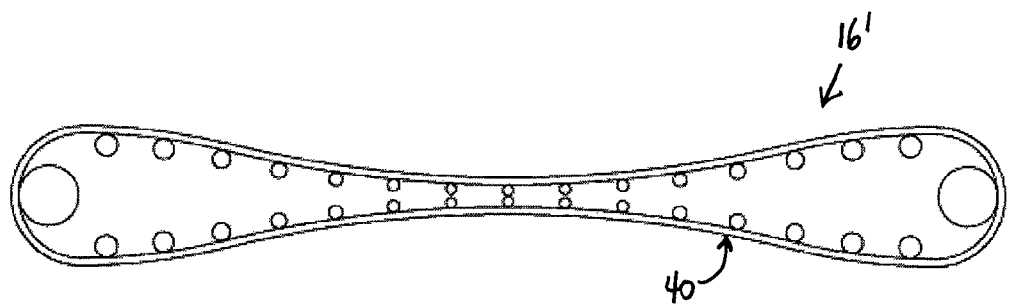
FIG. 10 is a cross-sectional view taken across line X-X of the instrument channel of FIG. 6 in a first collapsed configuration showing another embodiment of a plurality of stiffening elements extending therethrough.

The instrument channel can include various additional features to facilitate movement between the first and second configurations. In one embodiment, the instrument channel can include one or more stiffening elements extending longitudinally along the instrument channel for providing longitudinal strength to help prevent inversion of the channel during instrument removal, while still allowing for radial flexibility of the channel. The stiffening elements can be formed at any location along the instrument channel, including along inner and outer surfaces or within the sidewall, and they can extend along the entire length of the channel or along any portion thereof in order to facilitate prevention of inversion of the instrument channel. The stiffening elements can have a variety of configurations. In one exemplary embodiment, the stiffening elements are in the form of a plurality of surface features 40, shown in a cross section of the twisted instrument channel 16' in FIGS. 9-10. The surface features 40 can be formed in the instrument channel in a variety of ways, including being molded and extruded in the inner wall of the instrument channel 16'. The surface features 40 can be, for example, in the form of elongate ridges that extend longitudinally along the instrument channel 16'. The surface features 40 can also aid in controlling movement of the instrument channel between the collapsed and expanded configurations. For example, FIG. 9 illustrates two larger surface features 40a disposed on opposed sides of the channel 16', and a plurality of smaller surface features 40b positioned along the planar sidewalls such that the larger surface features 40a have a greater stiffness than the smaller surface features 40b. As a result, the sidewalls can more easily compress and expand relative to one another. FIG. 10 illustrates another embodiment in which the surface features 40 along the planar sidewalls decrease in cross-sectional diameter towards the midpoint of the sidewall. As illustrated, the decreasing cross-sectional diameter of the surface features 40 allows the planar sidewalls to compress toward one another, thus facilitating a tighter seal through the instrument channel 16' when the channel 16' is in the first collapsed configuration. In addition to facilitating movement between the first and second configurations, the surface features 40 can also reduce friction between the instrument channel 16' and the instrument inserted therein as the instrument only comes into contact with the surface features 40 and not the entire inner surface of the instrument channel 16'. A person skilled in the art will appreciate that the shape, size, and location of the stiffening elements can be optimized to achieve a desired result.

Figure 11:
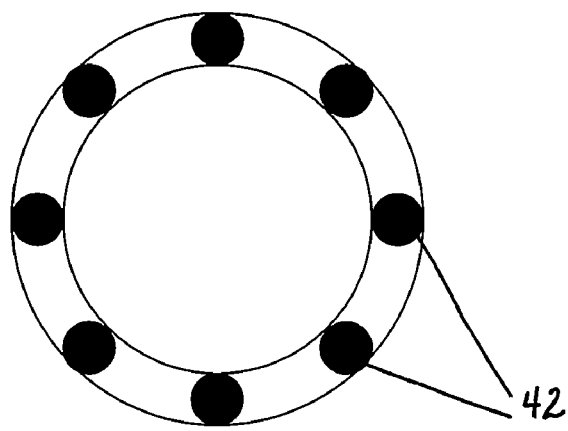
FIG. 11 is a cross-sectional view of an instrument channel in an expanded configuration showing a yet another embodiment of a plurality of stiffening elements extending therethrough.
Figure 12:
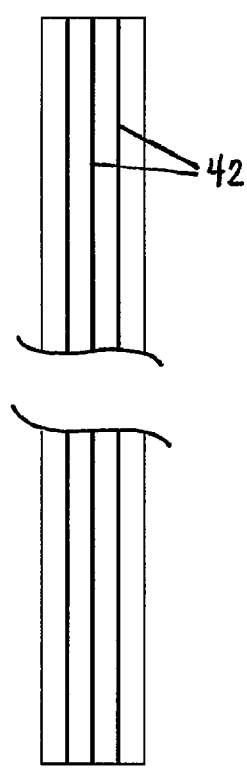
FIG. 12 is a longitudinal cross-sectional view of the instrument channel of FIG. 11 showing the stiffening elements extending therethrough.

In another embodiment shown in FIG. 11, the stiffening elements can be in the form of longitudinal grooves or channels 42 formed in the wall of the instrument channel and having springs and/or wires disposed therein that are adapted to prevent inversion of the channel. In one embodiment, the springs and/or wires can be pre-stressed such that the springs and/or wires are naturally in the first collapsed configuration to help facilitate movement from the second expanded configuration back to the first collapsed configuration. A person skilled in art will appreciate that any number of stiffening elements can be used. Further, similar to the surface features 40 shown in FIGS. 9-10, the size and shape of the longitudinal grooves can be varied to vary the cross section of the instrument channel.

The present invention also provides methods for accessing a body cavity. In one exemplary embodiment, an opening can be formed in tissue, for example, in the abdominal wall or umbilicus, and the retractor 58 can be positioned within the opening to engage the tissue between its proximal and distal flanges thereby forming a pathway through the tissue. In one exemplary embodiment, the proximal flange of the retractor 58 can be positioned on an external tissue surface, and the distal flange of the retractor 58 can be positioned on an internal wall of the body cavity. As a result, the housing 54 will rest against the external tissue surface, and the instrument channel (s) will extend from the retractor 58 into the body cavity, e.g., the abdominal cavity. A surgical instrument can be passed through an access port 14 in the housing 54 of the device 10 and into the instrument channel extending therefrom. As the instrument is moved through the instrument channel, it will force the channel to move from the natural resting state in a first collapsed configuration in which the instrument channel is sealed, for example, either curled as in the instrument channel 16 or twisted as in the instrument channel 16', to a second expanded configuration, for example, the uncurled or untwisted state. As the instrument is being inserted, the instrument channel can collapse around the instrument to form a seal therearound. A sealing element(s) located in the housing and/or instrument channel can additionally or alternatively form a seal around the instrument inserted therethrough. The instrument can be passed into the channel until a distal end of the instrument extends distally from the distal end of the instrument channel to allow the instrument access to the body cavity to perform a procedure therein. The instrument can then be removed from the instrument channel, during which the instrument channel will either curl or twist as the instrument is being removed to create a seal. Longitudinal stiffening elements formed in the instrument channel can help prevent inversion of the instrument channel, for example, by preventing the instrument from pulling the instrument channel into the housing 54 when the instrument is being removed therefrom. Other exemplary embodiments of methods for performing gastrectomies are disclosed in U.S. patent application Ser. No. 12/242333 filed on even date herewith and entitled "Methods And Devices For Performing Gastrectomies And Gastroplasties," which is hereby incorporated by reference in its entirety.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical access device, comprising:
    a housing having at least one access port therein for receiving a surgical instrument therethrough;
    a retractor extending distally from a distal end of the housing and including an opening extending therethrough; and
    at least one elongate flexible instrument channel extending distally from a distal end of the retractor and having a lumen extending therethrough and in fluid communication with the at least one access port in the housing, the channel being adapted to move from a first collapsed configuration in which the channel is sealed to substantially prevent fluid from flowing therethrough to a second expanded configuration upon insertion of an instrument therethrough, the elongate instrument channel being in a natural resting state in the first collapsed configuration.

2. The device of claim 1, wherein the elongate instrument channel is twisted in the first collapsed configuration and untwisted in the second expanded configuration.

3. The device of claim 1, wherein the elongate instrument channel has a substantially planar cross section in the first collapsed configuration.

4. The device of claim 1, wherein the elongate instrument channel includes at least one sealing element disposed therein and configured to form a seal around an instrument inserted therethrough.

5. The device of claim 1, wherein the elongate instrument channel includes at least one stiffening element extending longitudinally therealong and configured to provide longitudinal strength to the channel for preventing inversion of the channel while allowing for radial flexibility of the channel.

6. The device of claim 1, wherein the retractor includes a proximal end coupled to the housing and a distal end coupled to a proximal end of the elongate instrument channel.

7. A surgical access device, comprising:
 a housing having an access port extending therethrough for receiving a surgical instrument; and
 an elongate flexible instrument channel extending from the housing and having an inner lumen extending longitudinally therethrough and in communication with the access port in the housing, the inner lumen including a plurality of stiffening elements extending longitudinally along the channel and configured to provide longitudinal strength to the channel for preventing inversion of the channel while allowing for radial flexibility of the channel;
 wherein at least one of the plurality of stiffening elements has a larger diameter than at least one other of the plurality of stiffening elements.

8. The device of claim 1, wherein the housing includes a plurality of access ports therein.

9. The device of claim 8, wherein the at least one elongate flexible instrument channel comprises a plurality of elongate flexible instrument channels extending from the retractor, each elongate instrument channel being axially aligned with one of the plurality of access ports.

10. The device of claim 1, wherein the at least one access port includes at least one seal therein and configured to form at least one of a seal within the access port when no instrument is disposed therein and a seal around an instrument inserted therethrough.

11. The device of claim 1, wherein the elongate flexible instrument channel can form a seal around instruments of various diameters.

12. The device of claim 7, wherein the elongate instrument channel is configured to increase in length in the longitudinal direction upon insertion of an instrument into the channel and decrease in length in the longitudinal direction upon removal of the instrument from the channel.

13. The device of claim 7, wherein the at least one stiffening element extends from a distal end to a proximal end of the elongate instrument channel along the elongate instrument channel.

14. The device of claim 7, wherein the at least one stiffening element is in the form of at least one longitudinally-extending surface feature.

15. The device of claim 7, wherein the at least one stiffening element comprises at least one wire.

16. The device of claim 7, wherein the at least one stiffening element comprises at least one spring disposed within a longitudinal groove formed in the channel.

17. The device of claim 7, wherein the elongate instrument channel is adapted to move from a first collapsed configuration in which the channel is sealed to substantially prevent fluid from flowing therethrough to a second expanded configuration upon insertion of an instrument therethrough.

18. The device of claim 7, further comprising a retractor coupled between the housing and the instrument channel and including an opening extending therethrough forming a pathway through tissue.

19. The device of claim 7, wherein the housing includes a plurality of access ports therein.

20. The device of claim 18, wherein each access port has an elongate flexible instrument channel longitudinally aligned therewith.

21. The device of claim 7, wherein first and second larger diameter stiffening elements are disposed on opposed sides of the channel, with a remainder of the plurality of stiffening elements positioned along planar sidewalls extending between the opposed sides of the channel.

22. The device of claim 6, wherein the proximal and distal ends of the retractor have a larger diameter than a central portion of the retractor for engaging tissue therebetween.

23. The device of claim 12, wherein the elongate instrument channel is configured to curl longitudinally upon removal of the instrument from the channel.

24. A surgical access device, comprising:
 a housing having at least one access port therein for receiving a surgical instrument therethrough; and
 at least one flexible elongate instrument channel extending from the housing and having a lumen extending therethrough and in fluid communication with the at least one access port in the housing, the elongate instrument channel being movable between a first collapsed configuration in which the channel is sealed to substantially prevent fluid from flowing therethrough and a second expanded configuration upon insertion of an instrument therethrough, the elongate instrument channel being in a natural resting state in the first collapsed configuration;
 wherein the elongate instrument channel is helically twisted about a longitudinal axis of the channel in the first collapsed configuration and untwisted in the second expanded configuration.

* * * * *